United States Patent [19]

Hiroshima et al.

[11] Patent Number: 4,602,212
[45] Date of Patent: Jul. 22, 1986

[54] METHOD AND APPARATUS INCLUDING A FLUX LEAKAGE AND EDDY CURRENT SENSOR FOR DETECTING SURFACE FLAWS IN METAL PRODUCTS

[75] Inventors: Tatsuo Hiroshima; Tetsuya Hirota, both of Hyogo, Japan

[73] Assignee: Sumitomo Metal Industries, Ltd., Osaka, Japan

[21] Appl. No.: 502,547

[22] Filed: Jun. 9, 1983

[30] Foreign Application Priority Data

Jun. 14, 1982 [JP] Japan ................. 57-102600
May 20, 1983 [JP] Japan ................. 58-89467
Jun. 7, 1983 [JP] Japan ................. 58-102274

[51] Int. Cl.$^4$ ............... G01N 27/82; G01N 27/90; G01R 33/12
[52] U.S. Cl. ............... 324/227; 324/232; 324/240; 324/262
[58] Field of Search ......... 324/227, 228, 232, 235, 324/219-221, 239-243, 262

[56] References Cited

U.S. PATENT DOCUMENTS

| | | | |
|---|---|---|---|
| 3,056,920 | 10/1962 | Herrald | 324/221 |
| 3,185,923 | 5/1965 | Sadofsky | 324/226 |
| 3,202,914 | 8/1965 | Deem et al. | |
| 3,271,664 | 9/1966 | Mountz et al. | 324/232 X |
| 3,359,495 | 12/1967 | McMaster | 324/235 |
| 3,401,332 | 9/1968 | McClurg et al. | 324/232 X |
| 3,538,433 | 11/1970 | Wood et al. | 324/232 X |
| 3,579,099 | 5/1971 | Kanbayashi et al. | |
| 3,612,987 | 10/1971 | Placke et al. | |
| 3,739,261 | 6/1973 | Renken | 324/232 |
| 3,875,502 | 4/1975 | Neumaier | 324/241 |
| 4,155,455 | 5/1979 | Spierer et al. | 324/232 X |
| 4,439,730 | 3/1984 | Kauffman | 324/232 |
| 4,477,776 | 10/1984 | Spierer | 324/232 X |
| 4,485,344 | 11/1984 | de Sivry et al. | 324/262 |
| 4,510,447 | 4/1985 | Moyer | 324/240 |

FOREIGN PATENT DOCUMENTS 744316 6/1980 U.S.S.R. ............... 324/240

OTHER PUBLICATIONS

McMaster et al, "The Magnetic Reaction Analyzer . . . A New Tool for . . . and Control", paper presented at ASME Conference, Jan. 26, 1966, #66-PEM-5, pp. 1-13.

Primary Examiner—Gerard R. Strecker
Attorney, Agent, or Firm—Burns, Doane, Swecker and Mathis

[57] ABSTRACT

A technique for detecting flaws in a metal product which uses a combined eddy current and magnetic flaw detection technique. A first magnetic field having flux lines parallel to the surface of the test object and a second field having flux lines perpendicular to the surface of the test object are generated. The resultant magnetic field is affected by faults in the metal test object. A magnetic field detector adjacent the test object detects the resultant magnetic field and produces an output signal which is processed by a circuit to provide a pair of component signals representing the portion of the output signal corresponding to the individual components of the resultant magnetic field, thus providing an indication of the type of faults that are present in the test object. One, or both, of the individual magnetic fields can be generated by an electromagnet which is driven by an alternating current to thereby produce a rotary resultant magnetic field, thereby allowing greater flexibility in detecting all types of flaws.

19 Claims, 20 Drawing Figures

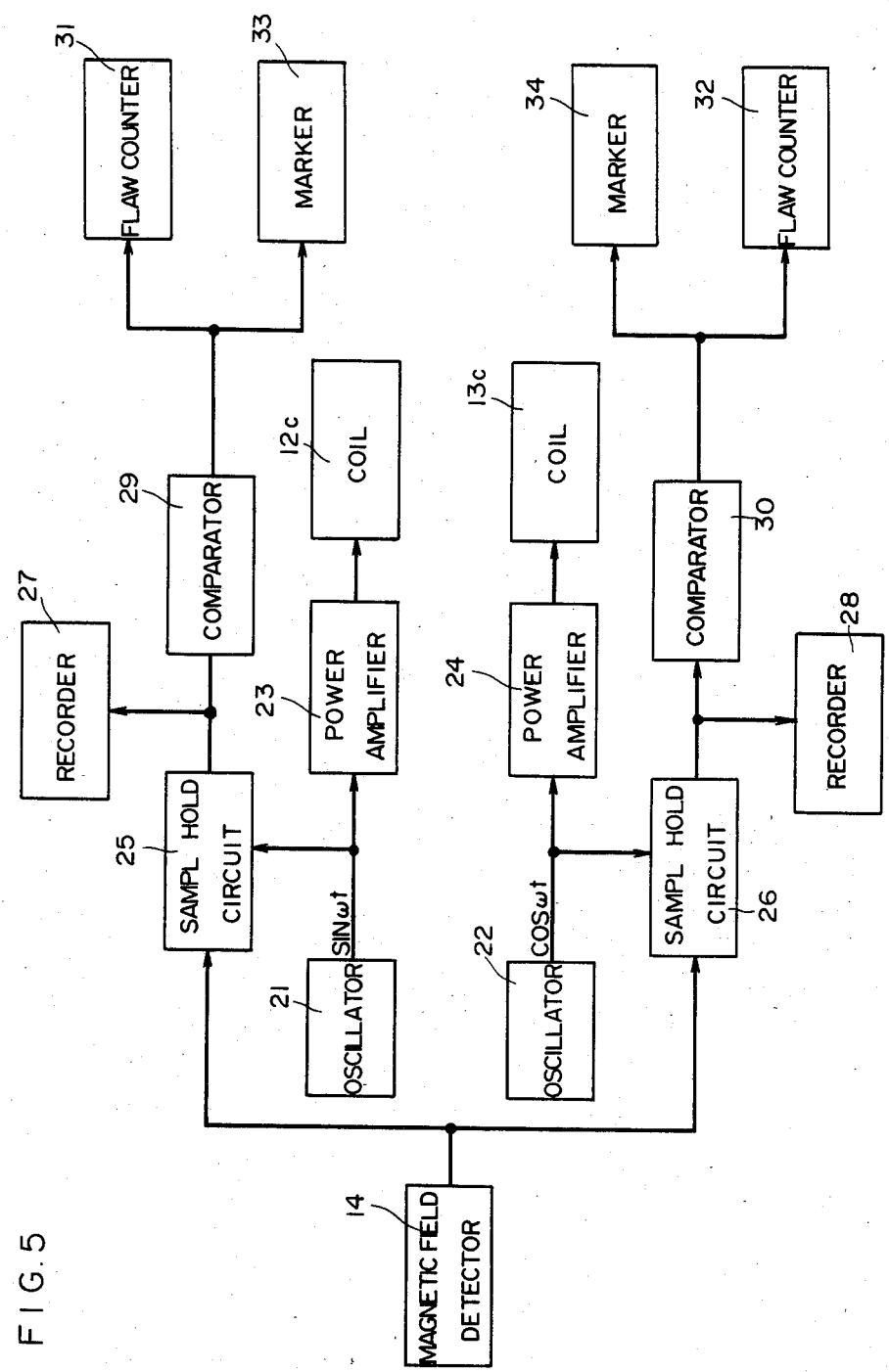
F I G. 5

METHOD AND APPARATUS INCLUDING A FLUX LEAKAGE AND EDDY CURRENT SENSOR FOR DETECTING SURFACE FLAWS IN METAL PRODUCTS

BACKGROUND OF THE INVENTION (1) Field of the Invention

This invention relates to a surface flaw detection method for a metal product and an apparatus for putting the method in practice.

(2) Description of the Prior Art

For detecting the surface flaws of a metal product, various nondestructive inspections have been put into practice, one or plural kinds of methods therefor having been applied corresponding to the flaws expected to exist. For example, a magnetic inspection method for detecting leakage flux generated from the surface of an object to be inspected is mainly used to detect flaws, such as cracks, expected to extend in the regular direction to some extent and the eddy current inspection method for the flaws, such as pits, extending merely in the direction of thickness of object. The magnetic inspection method generally is (1) superior in surface flaw detection for ferromagnetic substances, such as iron and steel products, (2) capable of detecting inherent flaws even not open at the surface, and (3) capable of inspecting the position and length of the flaw on the surface, but is defective in difficulty of detecting the internal flaws. On the other hand, the eddy current inspection method is advantageous in that (1) the detection result is obtained directly by an electric output, (2) the non-contact method permits rapid inspection speeds, (3) the method is suitable for detecting surface flaws and pit flaws, (4) the scope of applicability is wide because the inspection can follow the flaws, variation in object, and dimensional change, and (5) the signal and the flaw volume have an approximately proportional relation, but is defective in that (1) the method is not applicable unless the material form is simple, (2) a flaw positioned deep under the surface is not detectable, and (3) the influence of material factor other than the object to be tested often causes noises.

Also, the magnetic inspection method is effective in magnetization perpendicular to the flaw, but it is impossible to detect flaws when the magnetization is in the same direction as the flaw because no magnetic pole is generated at the flaw and the leakage flux from the surface of object to be inspected is minute. At present, however, the following method of utilizing a plurality of magnetic fields has become possible to detect the flaws irrespective of the direction of flaw.

For example, a round steel bar 1, as shown in FIG. 1, is directly axially energized to be magnetized circumferentially and a current flows in a coil around the steel bar 1 to magnetize the bar 1 axially, so that the circumferential magnetization detects the surface flaws 1a extending circumferentially of the bar 1 and the axial magnetization detects those flaws 1b axial of the same, which has been well known.

Also, an inspection method as shown in FIG. 2 has been well known which comprises a pair of coils 2, 2 surrounding a pipe 1' and a magnet 3 having opposite magnetic poles at both sides diametrical of pipe 1', the coils 2, 2 and magnet 3 being disposed in tandem, so that the coils 2, 2 magnetize the pipe 1' axially thereof to thereby detect a circumferential surface flaw 1'b in the magnetic field by use of a magnetic field detector 2a and the magnet 3 magnetizes the same circumferentially thereof to thereby detect an axial surface flaw 1'a in the magnetic field by a magnetic field detector 3a.

The surface flaws on the metallic object, however, include the flaws called the pit flaws, as well as the cracks, the pit flaws being difficult to detect by the aforesaid magnetic detection. Hence, the detection of pit flaws, if necessary, should depend on the eddy current inspection method, the detection of crack-like flaws depending on the magnetic particle detection of high detection power. Therefore, there has been trouble such that a plurality of inspection methods are indispensable for use according to the kind of object to be inspected and to properties of the flaws.

OBJECTS AND BRIEF SUMMARY OF THE INVENTION

A first object of the invention is to provide a method and an apparatus for detecting surface flaws in metal products, which are capable of detecting at a time all the flaws irrespective of those open or not on the surface or the pit flaws, and the flaws, when viewed in the plane, are detectable irrespective of the extending direction of flaw.

A second object of the invention is to provide a method and an apparatus capable of detecting the surface flaws of metal products irrespective of configurations of the flaws in section in the direction of depth.

A third object of the invention is to provide a method and an apparatus for detecting surface flaws in metal products, which are capable of detecting surface flaws of various types and of discriminating properties of the flaws.

A fourth object of the invention is to provide a method and an apparatus for detecting surface flaws in metal products, which are capable of detecting surface flaws of various types on an object round in section to be inspected throughout the circumference and length.

A fifth object of the invention is to provide an apparatus for detecting surface flaws in metal products, which are capable of scanning and detecting at high speed the surface flaws of various types on an object having a flat surface, such as a steel bar square in section.

A sixth object of the invention is to provide an apparatus for detecting surface flaws in metal products, which are capable of scanning and detecting at high speed the surface flaws of various types on an object having a flat surface, such as a steel bar, and of discriminating the properties of detected flaws.

This invention is characterized basically in that a resultant magnetic field which is formed by field in the direction along and perpendicular to the surface of an object to be inspected is generated, and a magnetic field detector detects the resultant magnetic field comprising the leakage magnetic field from the surface flaws obtained by the component of said resultant magnetic field in the direction along the surface of said object to be inspected and the magnetic field related to an eddy current obtained on the surface of said object by the component perpendicular to said surface. Such inspection method differs from the conventional one of using plural magnetic fields like FIG. 1 and is unique in the flaw detection by the resultant magnetic field including the magnetic field perpendicular to the surface of object to be inspected, thereby enabling the flaw detection regardless of the direction and configuration of flaw.

The above and further objects and features of the invention will more fully be apparent from the following detailed description with the accompanying drawings.

BRIEF DESCRIPTION OF THE DRAWINGS

FIG. 5 is a schematic circuit diagram exemplary of magnetic field generator and detector circuits.

DETAILED DESCRIPTION OF THE INVENTION

Figure 1:
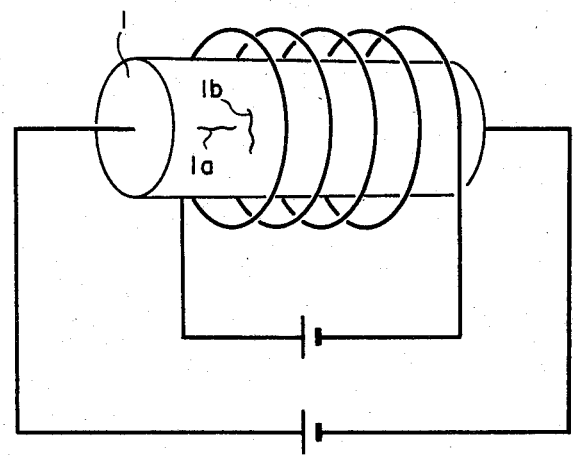
FIGS. 1 and 2 are views illustrating conventional flaw detection methods using a plurality of magnetic fields.
Figure 2:
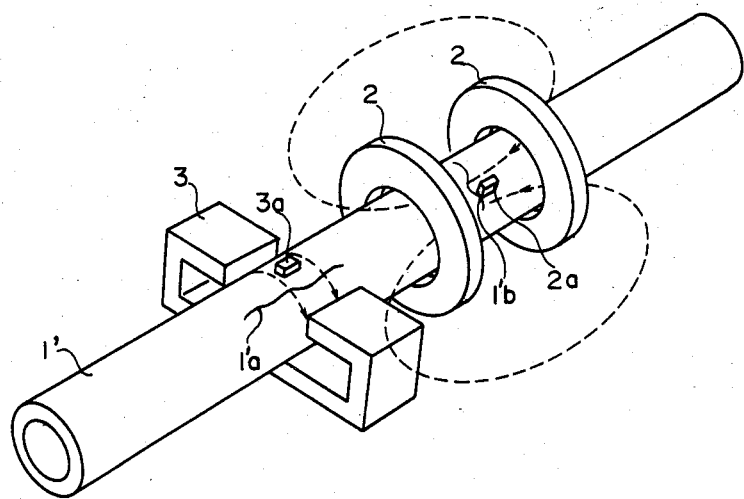
Figure 3:
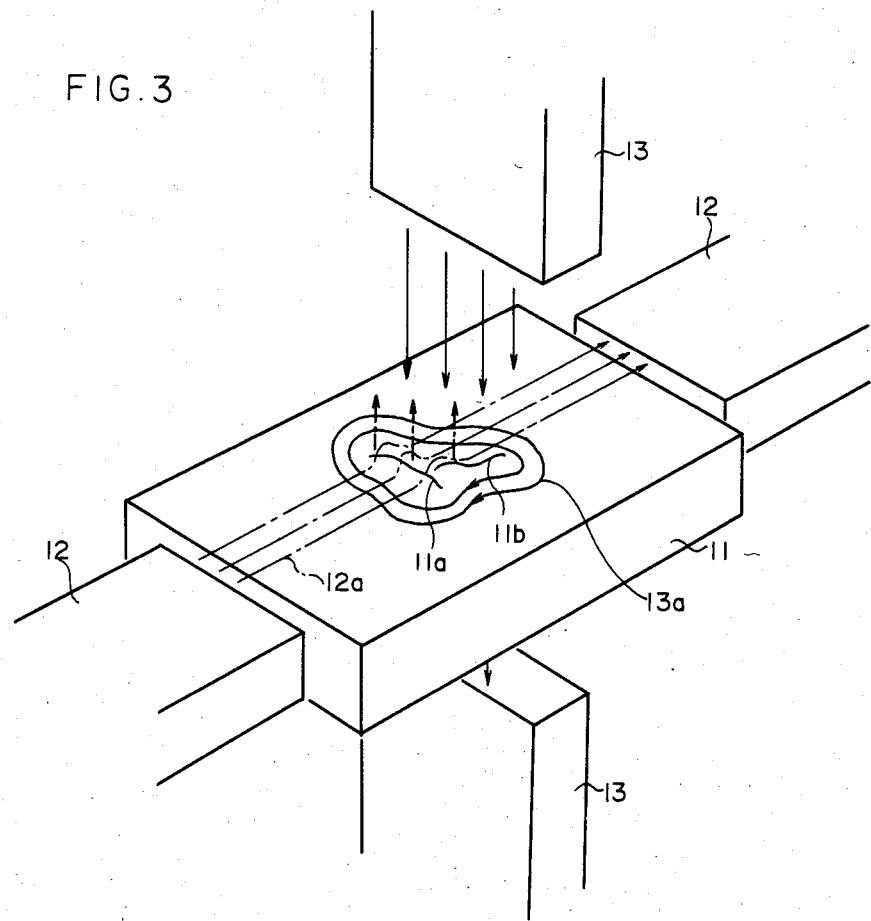
FIG. 3 is a view illustrating the principle of the flaw detection method of the present invention.

Referring to FIG. 3, magnetic field generators 12, 12 of the present invention are provided at opposite sides of an object 11 to be inspected in order to generate a magnetic field parallel to the surface of object 11, and magnetic field generators 13, 13 are arranged adjacent the top and bottom surfaces of object 11 to generate a magnetic field perpendicular thereto. A magnetic field detector 14 (FIG. 4) facing the surface of object 11 detects magnetic field produced by flaws present in a metal object positioned in the aforesaid magnetic fields.

The magnetic field generators 12, 12 produce a magnetic field corresponding to that for the conventional magnetic flaw detection and detect the leakage flux generated at the portion where a flaw 11a intersecting the magnetic flux 12a exists. Accordingly, the magnetic field generators 12 may generate a direct current magnetic field, but it is preferable to use a magnetic field generator generating an alternating current magnetic field, as discussed below. Thus, a rotary magnetic field is applied on the portion of material to be inspected to thereby perform the flaw detection not affected also by the flaws extending in the direction of depth of object 11.

On the other hand, the magnetic field generators 13, 13 generate an alternating current magnetic field to induce an eddy current 13a on the surface of object 11 to be inspected. The eddy current 13a, when the flaws 11a and 11b exist on the surface of object 11, is disturbed to cause turbulence in the magnetic field perpendicular to the surface of object 11, thus permitting detection of the flaws. Also, the flaw 11b parallel to the magnetic flux 12a can be detected by the turbulent magnetic field.

Only a single magnetic field detector of a single directivity need be used to enable detection of the magnetic field perpendicular to the surface of object 11. In this case, the magnetic field detector 14 serves to detect the component perpendicular to the surface of object 11, in the compound magnetic field produced by the flaws and the magnetic fields from the magnetic field generators 12 and 13, in which the detection signal indicates the existence of a flaw by the extent or variation of the level of the signal. The properties of the detected flaws can be discriminated by the signal process discussed below.

Figure 4:
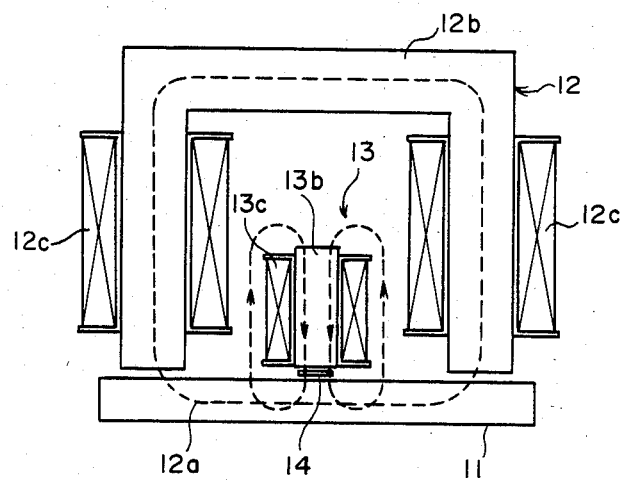
FIG. 4 is an elevational view exemplary of a combination of a magnetic field generator with a magnetic detector.

Next, a concrete construction in combination of two magnetic field generators 12 and 13 with the magnetic field detector 14 will be shown in FIG. 4. The magnetic field generator 12, which has an inverse U-shaped iron core 12b facing the surface of object 11 and coils 12c, 12c wound onto the legs of cover 12b to flow an alternating current into the same, is disposed to generate the magnetic flux parallel to the surface of object 11. The magnetic field generator 13, which has a bobbin 13b smaller in length than each leg of core 12b and a coil 13c wound around the bobbin 13b to flow an alternating current into the bobbin 13c, is disposed at the center between the legs of generator 12 to thereby generate the magnetic field perpendicular to the object 11. The magnetic field detector 14 is disposed at the end face of the magnetic pole of bobbin 13b at the object 11 side and faces the surface of object 11. Hence, the magnetic fields parallel and perpendicular to the surface of object 11 are generated at the portion of the surface of object 11 opposite to the magnetic field detector 14, thereby enabling the flaw detection under the aforesaid principle.

Next, explanation will be given of an electric circuit connected with the magnetic field generators 12 and 13 and the magnetic field detector 14 shown in FIG. 4. Referring to FIG. 5, an example of the electric circuit is shown, in which the magnetic field generators 12 and 13 each generate alternating current magnetic fields. In detail, oscillators 21 and 22 each generate a sine wave having an angular frequency $\omega$. The outputs of the oscillators 21 and 22 pass through the power amplifiers 23 and 24 and are supplied to the coils 12c and 13c, respectively, at the respective magnetic field generators 12 and 13 to generate the magnetic field. An output of magnetic field detector 14 is given to sample hold circuits 25 and 26. The sample hold circuits 25 and 26 also receive the outputs of oscillators 21 and 22 respectively so as to sample and hold the output from the magnetic field detector 14 in accordance with the timing related to phase of each oscillator output. The outputs of sample hold circuits 25 and 26 are recorded in recorders 27 and 28, given to comparators 29 and 30, and compared with a comparison reference value preset thereat respectively, so that when the output is larger than the reference value, a predetermined signal is generated as the flaw detection and counted by flaw counters 31 and 32 connected to the output terminals of comparators 29 and 30 and markers 33 and 34 are driven to apply paint marks on the portion corresponding to the position of the detected flaw. Since the magnetic field generators 12 and 13, magnetic field detector 14, and object 11 to be inspected, are moved relative to each other, the markers 33 and 34, as in the conventional apparatus, are driven at the proper moment as the portion including the detected flaw leaves the detection zone of magnetic detector 14 after the flaw detection therewith.

The oscillators 21 and 22 are driven in association with each other to allow the oscillation outputs thereof to have a predetermined phase relation. Now, assuming that the oscillation outputs are different in phase by an angle of 90°, the output of oscillator 21 is represented by sin ωt and that of oscillator 22 by cos ωt, whereby in a case where the sample hold circuits 25 and 26 carry out sampling with the timing for taking the peak values of the outputs sin ωt and cos ωt of oscillators 21 and 22 respectively, the flaw detection being performable at the maximum sensitivity. In other words, regarding the oscillator 21 side, the leakage flux from the flaw is detected by a high S/N ratio in accordance with the timing for the strongest magnetic field, resulting in that the crack flaw detection signal (not detectable of the flaw parallel to the flux 12a) from the magnetic field by the magnetic field generator 12 is counted by the flaw counter 31, the marker 33 applying the mark corresponding to the counted value.

Similarly, at the line of oscillator 22, in a case where the eddy current generated by the magnetic field formed by the magnetic field generator 13 is disturbed by the flaw, the turbulent magnetic field can be detected by a high S/N ratio in accordance with the timing for the largest turbulence of magnetic field and the result of detection is counted by the flaw counter 32 and marked by the marker 34. The oscillator 22 detects the turbulence of the field caused by the eddy current, so that crack flaws in the various directions as well as the pit flaws are detected to thereby enable discrimination of the crack flaw at least intersecting the magnetic flux 12a generated from other flaws. In consideration of the information of the flaw existing on the object 11, the outputs of sample hold circuits 25 and 26 (the recording contents in recorders 27 and 28) can perform further detailed discrimination.

Figure 6:
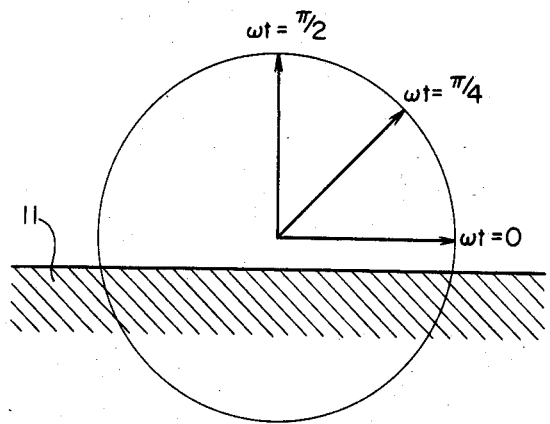
FIG. 6 is a view explanatory of a rotary magnetic field.

In a case where the outputs sin ωt and cos ωt of oscillators from the magnetic fields as abovementioned, the magnetic fields generated by the magnetic field generators 12 and 13 intersect perpendicularly to each other, whereby the resultant magnetic field of the same becomes a rotary magnetic field rotating in a cycle period of 2π/ω. The rotar magnetic field, as shown in FIG. 6, rotates around a point just under the magnetic field generator 13 in the vicinity of the surface of object 11 and varies in parallel to the surface of object 11 at phase of ωt=0, upwardly slantwise of the same at an angle of 45° in phase of ωt=π/4, and perpendicular to the same in that of ωt=π/2.

Figure 7:
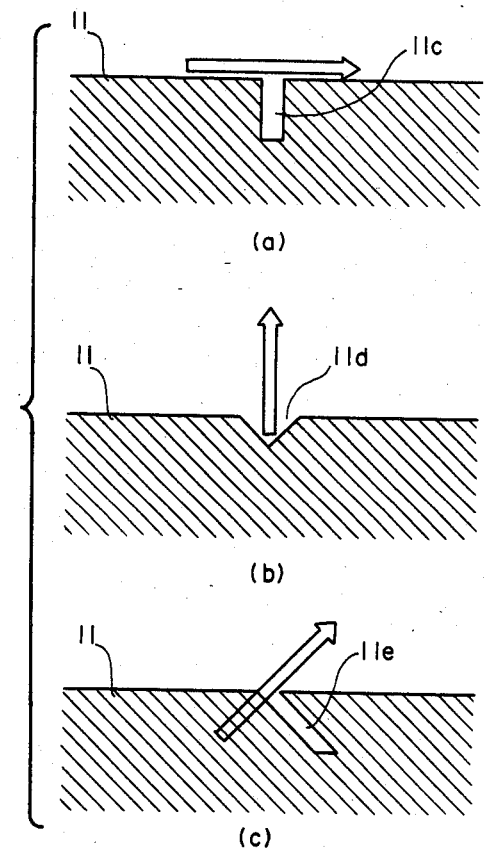
FIG. 7 is a view illustrating the relation between the rotary magnetic field and the kind of flaw.

In a case where an open-groove-like flaw 11c perpendicular in section to the surface of object 11 is placed in the magnetic field parallel to the surface thereof, as shown in FIG. 7(a), the component of leakage flux perpendicular to the surface of object 11 becomes maximum. Similarly, in a case where a flaw 11d of a V-like shape in section is placed in the magnetic field perpendicular to the surface of object 11, the same becomes maximum, and in a case where a flaw 11e of a groove-like shape in section slantwise to the surface of object 11 is placed in the magnetic field perpendicular to the direction of depth of the flaw slantwise to the surface, the same becomes maximum. Hence, the sample hold need only be carried out in phase corresponding to the flaw existing in the object 11 or required to be inspected, for example, when the slant flaw in FIG. 7(c) is assumed to be detected, the sample hold is carried out in accordance with the timing for ωt=π/4 and 5π/4, such flaw can be detected by a high S/N ratio.

In brief, the output of magnetic field detector 14 is picked up in connection with the phase of magnetic fields generated by the magnetic field generators 12 and 13, whereby the flaws of various forms in depthwise section can be detected and also the forms can be discriminated by charging the pick-up timing.

Alternatively, the phase difference between the outputs of oscillators 21 and 22 is not limited to 90°, but may be set at any desirable phase angle.

The intensity of magnetic field, when the phase difference is set to an angle of 90° or 270°, is equal in every angular direction, but can, at an angle other than the above, be increased in a particular direction, whereby it is preferable to decide the phase difference corresponding to the sectional form of the flaw to be detected in the direction of depth thereof.

Figure 8:
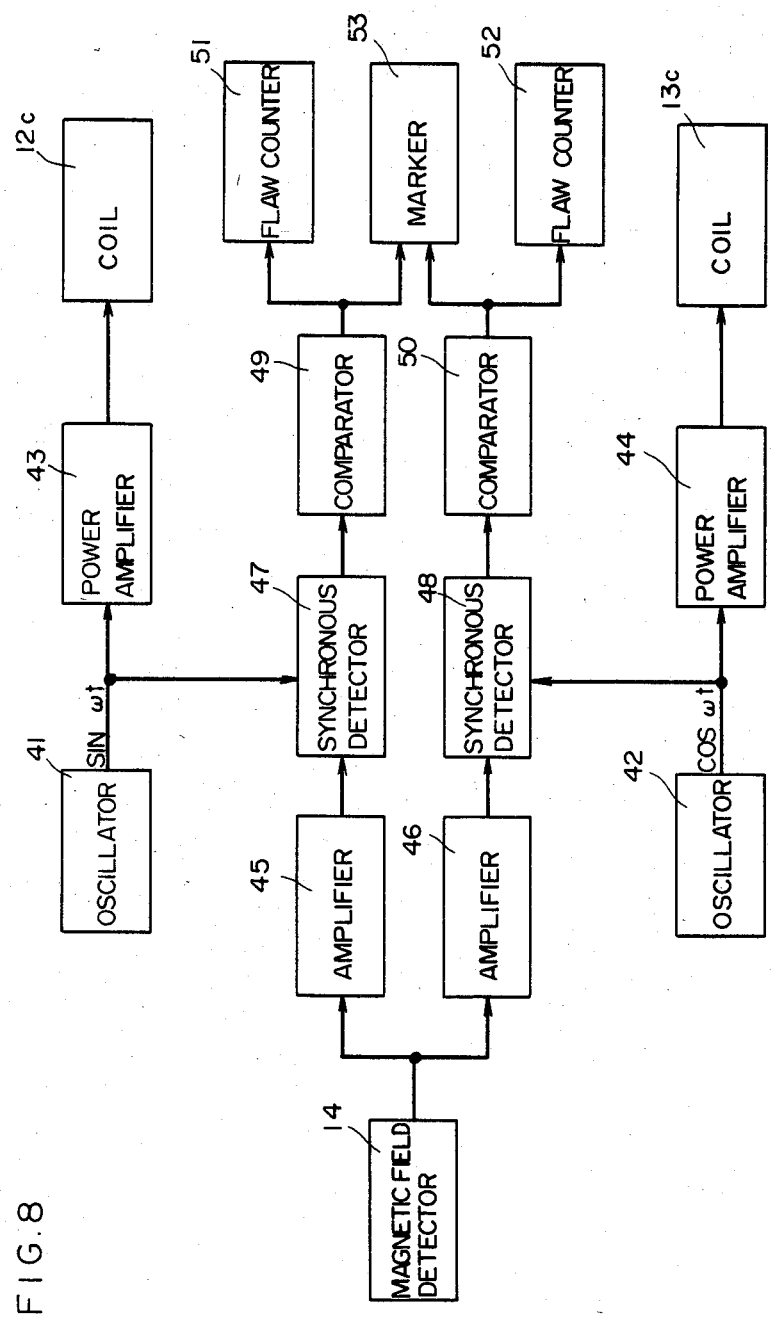
FIG. 8 is a schematic circuit diagram of a modified embodiment of the magnetic field generator and detector circuit.

FIG. 8 shows an electric circuit of another modified embodiment of the flaw detection apparatus of the invention, in which an oscillator 41 of angular frequency of ω is adapted to generate one magnetic field and an oscillator 42 of angular frequency of mω is adapted to generate the other magnetic field. In detail, the output sin ωt of oscillator 41 is given to a power amplifier 43 and amplified thereby to be supplied to the coil 12c of magnetic field generator 12, thereby forming the magnetic field parallel to the surface of object 11 to be inspected. The output sin mωt of the other oscillator 42 is given to a power amplifier 44 and amplified thereby to be supplied to the coil 13c of magnetic field generator 13, thereby forming the magnetic flux perpendicular to the surface of object 11. The outputs of both the oscillators need only be different (m≠1) in frequency, the value of m being not particular, but preferably being two or more because the different frequencies aim at discrimination of signal component on the basis of both the magnetic fields.

The output signal of magnetic field detector 14 is given to synchronous detectors 47 and 48 through amplifiers 45 and 46 respectively. The synchronous detectors 47 and 48 also receive the outputs from oscillators 41 and 42, respectively, to thereby carry out phase detection related to the oscillation outputs of the same. Hence, the leakage flux caused by the flaws in the magnetic field generated by the magnetic field generator 12 is fetched by the synchronous detector 47 and the turbulence caused by the flaw in the magnetic field generated by the generator 13 is fetched by the synchronous detector 48, so that the outputs of synchronous detectors 47 and 48 are fed into comparators 49 and 50 and compared with the comparison reference values preset therein respectively. When the outputs of the synchronous detectors 47 and 48 are larger than the reference values preset in comparators 49 and 50, respectively, they are counted as a flaw detection separately by flaw counters 51 and 52 and marked by a common marker 53, where the marker may of course be separate.

Thus, the frequency for magnetization is made different to enable flaw detection in connection with each magnetic field, resulting in the discrimination of the kind of flaw. Also, for the different frequency, it is possible to generate the rotary field by oscillation in connection with each phase, whereby the flaw detection is performable irrespective of the form of flaw in section in the direction of depth.

Figure 9:
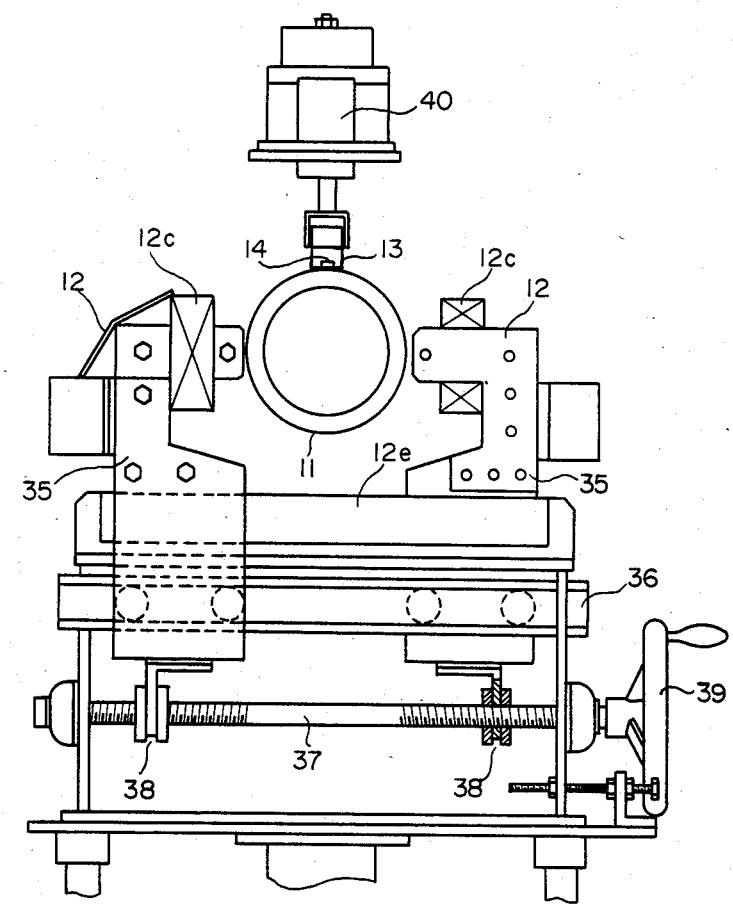
FIG. 9 is an elevational structural view of an apparatus for applying the invention to a steel pipe.

Referring to FIG. 9, an apparatus applying this invention is shown, in which pipe 11 to be inspected is moved lengthwise thereof and rotates around the axis. At both lateral sides of the area in which the object 11 is conveyed, the magnetic poles of the magnetic field generator 12 supported by slide members 35, 35 and magnetically coupled by a yoke 12 are provided opposite to each other, the coils 12c, 12c at the poles being energized by a power source (not shown) to form the magnetic field. A greater part of magnetic flux thereof passes through the object 11 to be put in an equalized condition to the magnetic field generated circumferentially of the object 11. The slide members 35, 35 are supported on a rail 36 at both lengthwise sides thereof and freely movable lengthwise of the rail 36, the rail 36 being disposed horizontally and perpendicularly to the moving direction of the object 11. A threaded feed rod 37 is provided under and parallel to the rail 36, and has at each end portion screw threads screwing reversely to each other. The screw threads are engaged by nut members 38, 38 fixed to the slide members 35, 35 respectively, so that a control wheel 39 fixed to one end of threaded feed rod 37 is rotated normally or reversely to allow the poles at the magnetic field generator 12 to move toward or away from the object 11 to an equal extent. Above the transfer area of the object 11 is mounted on air cylinder 40 which is directed downwardly and provided at the lower end with the magnetic field generator 13 and magnetic field detector 14, which are constructed as shown in FIG. 4. The magnetic field generator 13 forms the magnetic field radial with respect to object 11, whereby the magnetic field parallel to the surface of object 11 and that perpendicular thereto are produced just below the magnetic field detector 14, thus enabling the aforesaid flaw detection. The air cylinder 40 is controlled to adjust the position of the magnetic field generator 13 and detector 14, and the threaded feed rod 37 is rotated to adjust the position of the magnetic generator 12 to thereby allow the apparatus to adjust the objects of various diameters to be inspected.

Figure 10:
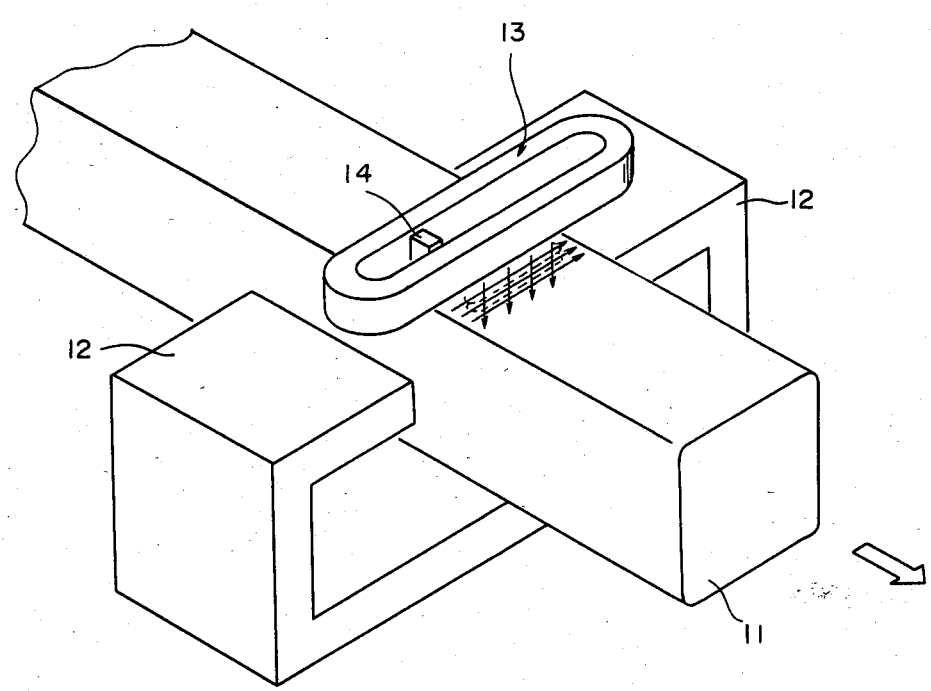
FIG. 10 is a structural view exemplary of an apparatus for applying this invention to a square steel bar.

Next, FIG. 10 shows an apparatus applied with this invention to detect flaws in an object 11, which is square in section, such as a steel bar or square steel. Generally, if the magnetic field generators and detector in assembly therewith as shown in FIG. 4 are moved perpendicularly to the transfer direction of the moving object 11, the surface thereof is inspected in a zig-zag manner, but such combination is heavy due to the iron core, whereby the apparatus moving in reciprocation becomes large-sized and also is difficult to move quickly, resulting in a low inspection speed. The apparatus in FIG. 10, however, has eliminated such defect.

The apparatus is so constructed that a magnetic field generator 12 having the magnetic poles opposite to each other at both sides of the transfer area of object 11 generates the magnetic field parallel to the test surface. A magnetic field generator 13 provided opposite to the surface to be inspected and comprising a substantially rectangular air-core coil of larger inner size than a width of the surface to be inspected generates the magnetic field perpendicular thereto, and a magnetic field detector 14 positioned within the coil of generator 13 is moved in reciprocation widthwise of object 11. In brief, the magnetic field generators 12 and 13 are stationary and only the light-weight detector 14 is moved.

Figure 11:
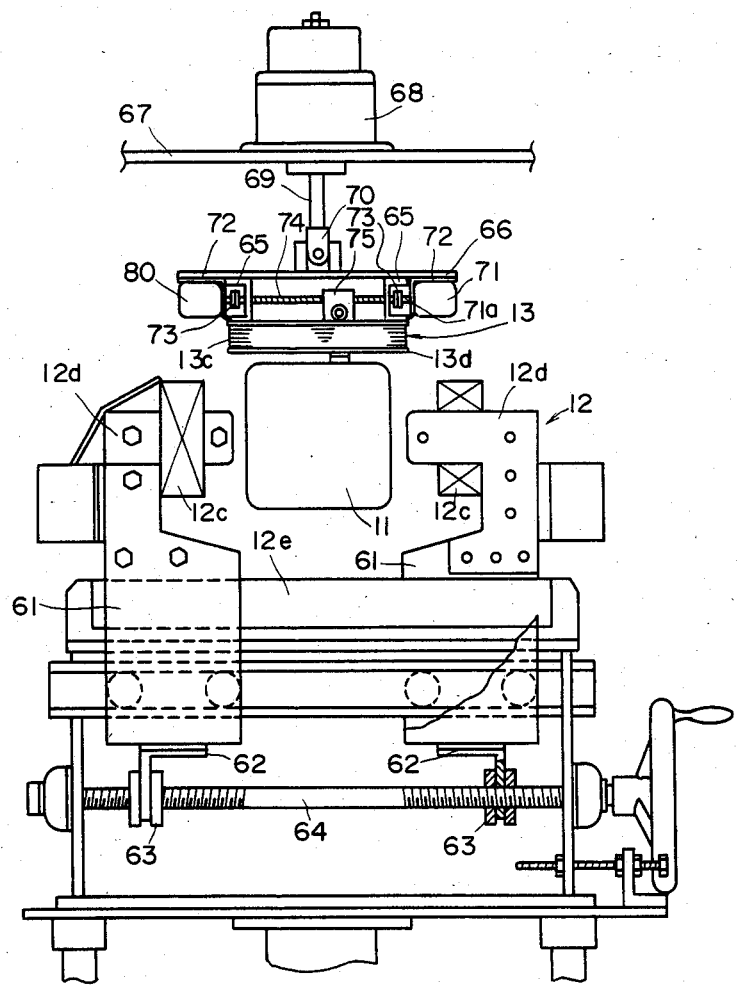
FIG. 11 is an elevational view of concrete construction in the FIG. 10 apparatus.

Next, the aforesaid apparatus will be described in accordance with FIGS. 11 and 12.

At both sides of the transfer area for the longitudinally moving test object 11 which is square in section is provided a magnetic field generator 12 for generating the magnetic field along the surface (upper surface) of object 11 to be inspected, the generator 12 having cores 12d, 12d around which coils 12c, 12c are wound and a yoke 12e under the object 11 and extending widthwise thereof, the cores 12d, 12d in part being movably supported on the yoke 12e by support plates 61, 61 respectively.

Moving bases 62, 62 are mounted to the lower ends of support plates 61, 61, nut members 63, 63 are mounted to the lower surfaces of moving bases 62, 62 and engage the threaded portions at both ends of a threaded shaft 64 bridged widthwise of object 11 and having screw threads reverse to each other respectively, so that the shaft 64 rotates normally or reversely to slide each core 12d on the yoke 12e widthwise of object 11, the cores 12 moving toward or away from the object 11.

A magnetic field generator 13 for generating the magnetic field perpendicular to the surface of object 11 to be detected is provided above the surface. The magnetic field generator 13 uses an air-core coil comprising a hollow elliptic coil bobbin 13d extending widthwise of object 11 and a coil 13c wound around the bobbin 13d, the air-core coil being mounted at the upper surfaces of both ends to the lower surface of U-shaped mounting members 65, 65 respectively, the upper surfaces of the mounting members 65, 65 being mounted to the lower surfaces of a follower mechanism support plate 66. A cylinder support plate 67 is provided on the follower mechanism support plate 66 and carries at the upper surface a cylinder 68 supporting its piston rod 69 downwardly. The piston rod 69 perforates the cylinder support plate 67 and supports at the utmost end the follower mechanism 66 at the upper center thereof through a universal joint 70 to thereby allow the support plate 66 to freely move slantwise with respect to the piston rod 69. The follower mechanism support plate 66 is provided with rollers (not shown) at the lower surfaces of upstream and downstream side portions in the transfer direction of object 11. The rollers are provided at both widthwise sides of object 11 to come into rotatable contact therewith and follow bends thereof.

At the lower surface of one side of the support plate 66 in the direction of width of object 11 is mounted a motor 71 through an L-shaped fixture 72. An output shaft 71a of motor 71 extends inwardly and is connected at the utmost end with a coaxial threaded rod 74 by coupling 73, the rod 74 being journalled through bearings at both ends thereof to the mounting members 65, 65 so as to rotate normally or reversely by the normal or reverse rotation of motor 71. Also, the threaded rod 74 engages the upper portion of a detector holder casing 75 so that the casing 75 moves on the threaded rod 74 widthwise of object 11 following the normal or reverse rotation of rod 74.

Figure 12:
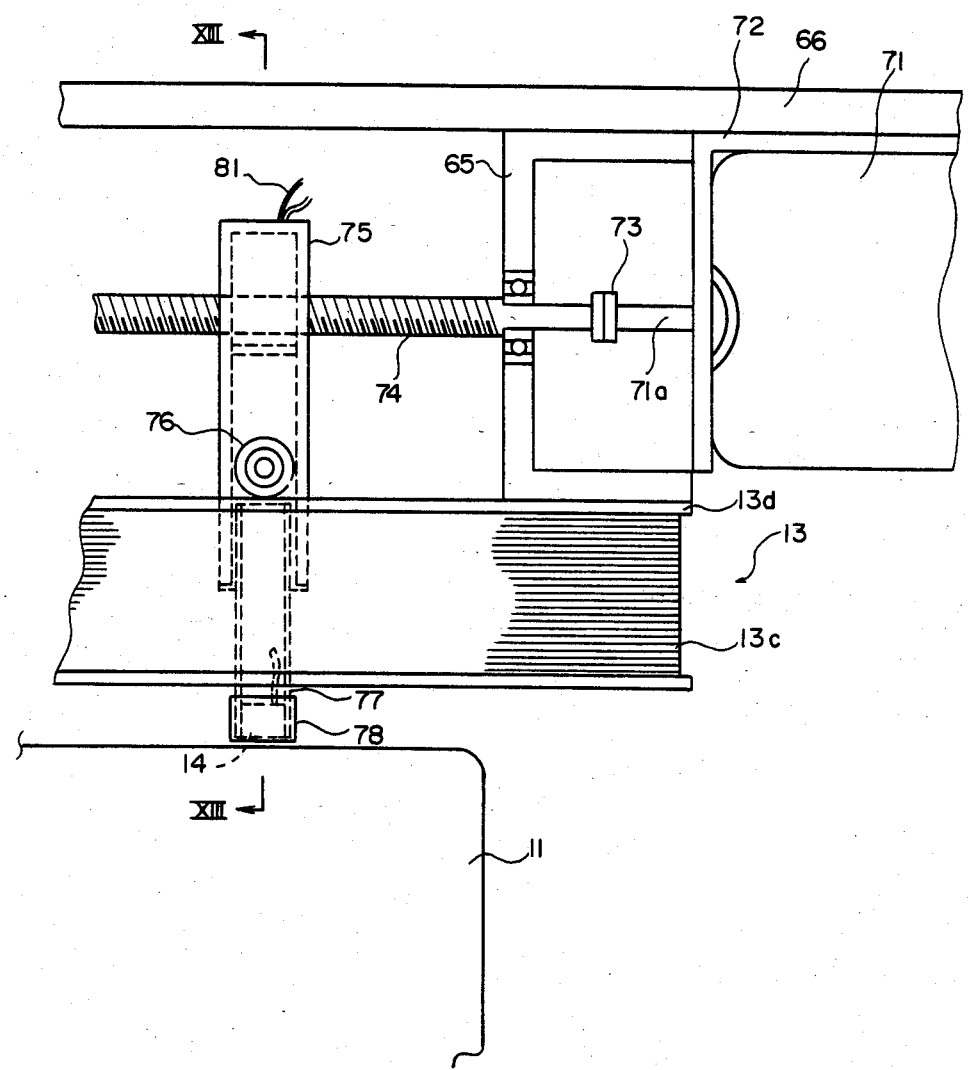
FIG. 12 is an enlarged view illustrating the mounting structure for the magnetic field detector of the FIG. 11 embodiment of the present invention.
Figure 13:
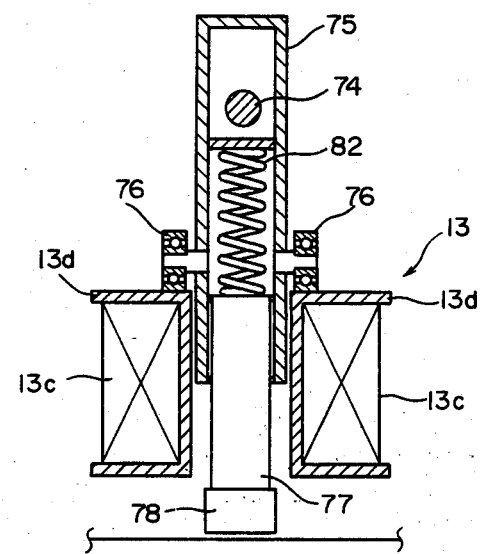
FIG. 13 is a sectional view taken on the line XIII—XIII in FIG. 12.

FIG. 13 is a sectional view taken on the line XIII—XIII in FIG. 12, in which the lower portion of casing 75 is positioned in the cavity in the coil bobbin 13d of magnetic field generator 13. Guide rollers 76, 76 are in rotatable contact with the upper surface of coil bobbin 13d and are mounted to the upstream and downstream sides of casing 75 so as to move in rotatable contact with the coil bobbin 13d as the casing 75 moves and also restrict the casing 75 from twisting caused by rotation of threaded rod 74. The casing 75 is open at the lower end face, through which opening the upper end of a detector holder 77, carrying the magnetic field detector 14 at the lower end, is inserted slidably into the casing 75 into which a compression spring 82 is arranged to push the holder 77 downwardly. The magnetic field detector 14 is fitted into the lower end portion of detector holder 77 and directed at the detection surface downwardly (toward the object 11), the detector holder 77 being covered at the lower end with a shoe 78 so that the detection surface of detector 14 is brought into contact with the detected surface of object 11 by the shoe 78.

The threaded rod 74 is rotatably supported at the end opposite to the motor 71 mounting side through a bearing to a mounting member 65. The rod 74 is connected by a coupling 73 to a position detector 80 using a potentiometer or a rotary encoder, the position detector 80 being mounted to the follower mechanism support plate 66 through an L-shaped fixture 72 so that the position of the magnetic field detector 14 moving by the normal or reverse rotation of threaded rod 74 is detected by the detector 80 relative to the width of object 11. In addition, reference numeral 81 in FIG. 12 designates a lead wire to transfer the signal between the magnetic field detector 14 and the signal processor.

Next, explanation will be given on operation of the apparatus constructed as abovementioned. In FIG. 11, the threaded shaft 64 at first is rotated to adjust the distance between the cores 12d, 12d of the magnetic field generator 12 in accordance with the width of object 11 transferred, and then the rod 69 at cylinder 68 is retracted to keep the magnetic field generator 13 and detector 14 in a safe area above the transfer region of object 11, the magnetic field generators 12 and 13 being energized. In such condition, the object 11 is transferred, and upon detecting by, for example, a detector using a photoelectric tube the entering of object 11 into the flaw detection zone of the apparatus of the invention, the piston rod 69 at cylinder 68 moves forward to allow the shoe 78 at the detector holder 77 to abut the detected surface of test object 11. The motor 71 is driven to rotate the threaded rod 74, so that the casing 75 carrying the detector holder 77 moves in the air-core portion of coil bobbin 13d widthwise of object 11 and the shoe 78 moves on the detected surface in slidable contact therewith, whereby the magnetic field detector 14 detects the compound magnetic field generated in the vicinity of the detected surface of object 11 to carry out the surface flaw detection on the object to be inspected.

Upon movement of a predetermined distance of casing 75 carrying the magnetic field detector 14 and others, the motor 71 is adapted to reversely rotate so as to move the casing 75 backwardly, thus moving it in reciprocation across the predetermined width in a zig-zag manner over the test surface of transferred object 11, the predetermined width being set corresponding to the width of object 11.

The guide rollers 76 mounted to the sides of casing 75 move on the upper surface of coil bobbin 13d in rotatable contact therewith to thereby smooth the movement of casing 75 and restrict the casing 75 from rotating together with the threaded rod 74.

Furthermore, at the upstream and downstream sides of magnetic field generator 13, rollers (not shown) are mounted to the follower mechanism support plate 66 to be in rotatable contact with the detected surface of object 11, the support plate 66 being freely movable slantwise by the universal joint 70 so that the detector holder 77 can follow a bend of object 11. Also, since the detector holder 77 is pushed downwardly by the compression spring 82, it follows the roughness at the detected surface without the possibility of damage to the holder.

Next, explanation will be given on a modified embodiment capable of detecting the flaws of various types throughout the overall circumference and length of an object round in section to be inspected.

Figure 14:
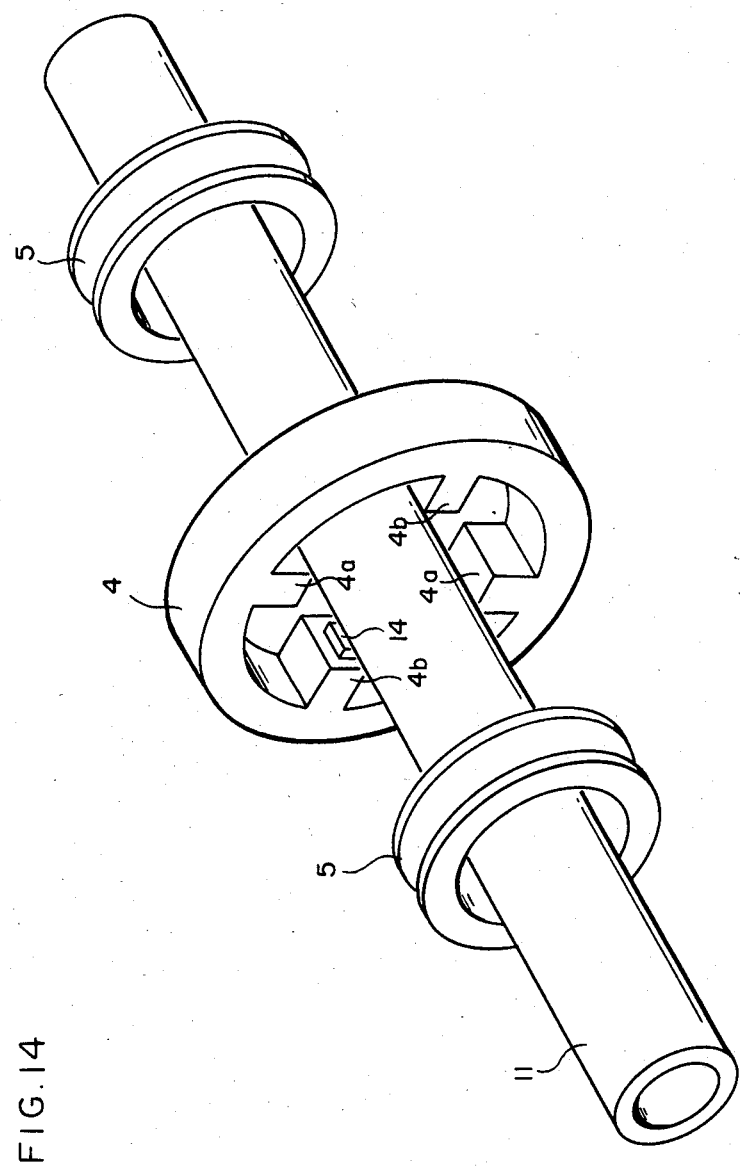
FIG. 14 is a view of another modified embodiment of the invention when applied to a steel pipe.
Figure 15:
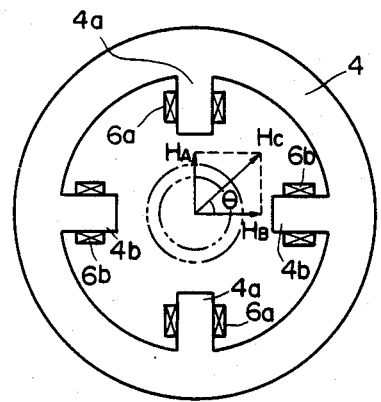
FIGS. 15 and 16 are views explanatory of the FIG. 14 embodiment.
Figure 16:
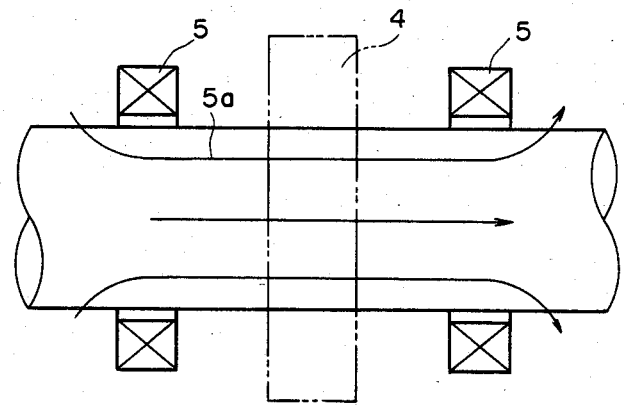

FIG. 14 is a perspective view of still another embodiment and FIGS. 15 and 16 are illustrations thereof, in which an annular electromagnet 4 for generating the alternating magnetic field concentrically with the test object 11 is provided within the transfer zone of object 11 (steel pipe) transferred lengthwise thereof. The electromagnet 4 has at the inner periphery four magnetic poles 4a and 4b at intervals of angle of 90°, the opposite poles 4a, 4a being wound by coils 6a, 6a and other opposite poles 4b, 4b by coils 6b, 6b respectively. An alternating current of $ia = Im \sin \omega t$ as the exciting current flows into the coils 6a, 6a on the poles 4a, 4a and an exciting current of $ia = Im \cos \omega t$ different from said alternating current in $\pi/2$ phase flows into the coils 6b, 6b on the poles 4b, 4b, thereby generating perpendicular intersecting magnetic fields whose intensity Ha and Hb change with the lapse of time. Hence, the compound magnetic field of both the fields changes in its direction with the lapse of time following the change of the intensity of both the fields. In other words, at the center of annular electromagnet, the field intensity Hc is constant due to a phase shift of alternating current and the rotary magnetic field of rotation speed $\omega t$ is formed. In brief, since it is considered that the virtual magnetic poles rotate, the eddy current generating position from the rotary magnetic field continues rotation. Accordingly, the magnetic field detector 14 facing the outer periphery of object 11 detects the turbulence of the magnetic field when a flow exists, thereby detecting the flaw. On the other hand, the object 11 is deemed to be magnetized circumferentially by the opposite magnetic poles 4a, 4a, or 4b, 4b, or virtual magnetic poles, so that the flaws in the direction of the flux, in turn in the direction perpendicular to the circumferential direction, are detected by the leakage flux caused by the flaws.

At the upstream and downstream sides of annular electromagnet 4 in the transfer direction of object 11 are provided annular solenoids 5, 5 through which the object 11 passes, the solenoids 5, 5 being energized to generate the circumferential magnetic flux 5a to form the magnetic field lengthwise of object 11, which magnetic field is formed at the overall outer periphery so that when a flaw extending intersecting with the flux 5a exists in any position at the outer periphery of object 11, the leakage magnetic flux is generated and detected by the magnetic field detector 14, thereby detecting the flaw. In addition, the annular solenoids 5, 5 may be given either AC or DC.

Figure 17:
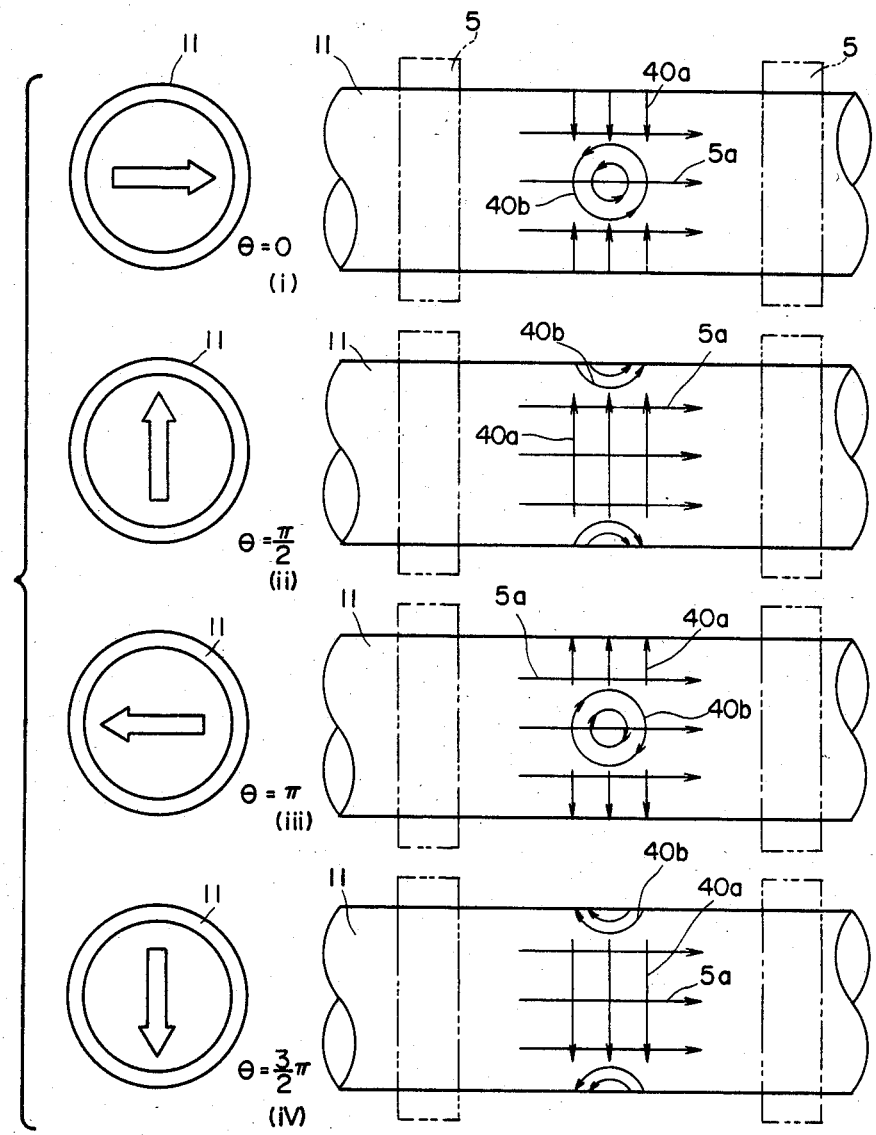
FIG. 17 is a view explanatory of the magnetic field in the FIG. 14 embodiment.

FIGS. 17(i) through 17(iv) are views exemplary of the direction of magnetic field, the magnetic flux generated at the outer periphery of object 11, and the eddy current induced in the rotary magnetic field. The annular electromagnet 4 generates on the outer periphery of object 11 the magnetic field 40a in the circumferential direction of the same and an eddy current 40b is induced in the vicinity of virtual pole in the rotary magnetic field, the annular solenoids 5, 5 generating the magnetic field 5a extending axially of object 11 on the outer periphery thereof. In the drawing, reference θ designates the direction of virtual pole on the basis of the direction of magnetic poles 4b, 4b as shown in FIG. 15. Accordingly, in a case where crack-like flaws axial and circumferential of object 11 exist on the outer periphery thereof, the magnetic field detector 14 detects the leakage field from the circumferential magnetic field 40a generated by the annular electromagnet 4 and the axial magnetic field 5a generated by the annular solenoids 5, 5, caused by the flaw. In a case where a pit-like flaws exist, the detector 14 detects the turbulence of magnetic field caused by the turbulent eddy current from the flaw, thereby detecting the flaws. The magnetic field detector 14 is rotated at lower speed than the rotational speed of rotary magnetic field so as to have the timing coincident with the virtual pole of rotary magnetic field at the position thereof, and scans spirally on the outer periphery of object 11 in cooperation with transfer of object 11, thereby performing the precise flaw detection throughout the outer periphery of object 11.

Figure 18:
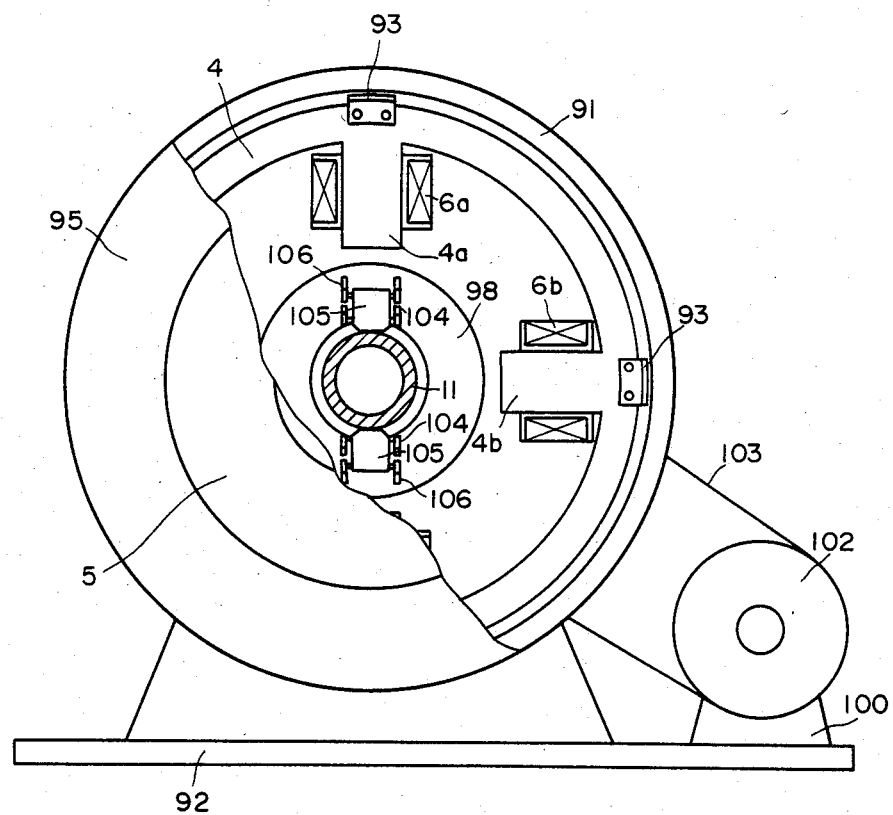
FIG. 18 is a partially cutaway elevational view showing a concrete construction of the same.
Figure 19:
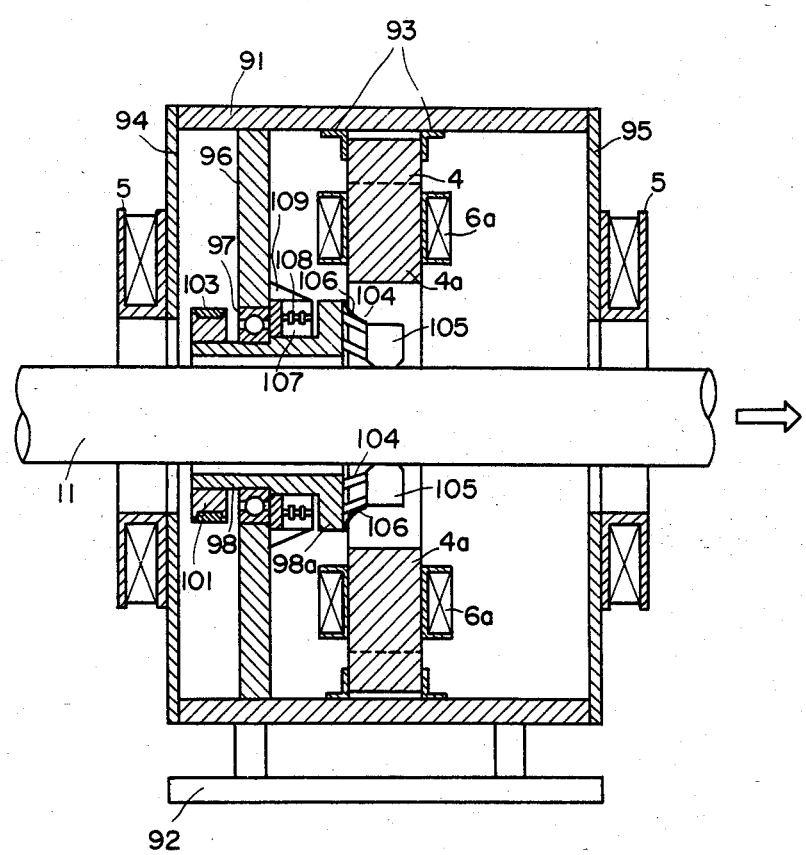
FIG. 19 is a longitudinal sectional view of the FIG. 14 embodiment.

FIG. 18 is a partially cutaway front view of a concrete embodiment of the invention and FIG. 19 is a longitudinal sectional view thereof, in which a cylindrical drum 91, in the transfer zone of object transferred lengthwise thereof, is fixed on a base 92 concentrically with the object 11. The drum 91 has an annular electromagnet 4 mounted thereto at an intermediate portion of the inner periphery, concentric with the drum 91, by bracket members 93. At the upper and lower and the right-hand and left-hand portions of annular electromagnet 4, two pairs of magnetic poles 4a and 4b project radially inwardly of the electromagnet 4 so that each magnetic flux perpendicularly intersects at the center thereof. The coils 6a and 6b are wound around the magnetic poles 4a and 4b respectively. Support discs 94 and 95, each having at the center a through bore concentric with the drum 91, are fixed to the end faces of the drum 91 at the upstream and downstream sides in the transfer direction of object 11, respectively. Annular solenoids 5, 5 are mounted concentrically at the outer peripheries of support discs 94 and 95 respectively.

A disc-like mounting plate 96 having at the center a round bore concentric with the drum 91 is fixed to the inner periphery of drum 91 between the annular electromagnet 4 and the upstream side support disc 94, the round bore rotatably supporting a cylindrical member 98 at an axially intermediate portion thereof through a bearing 97, so that the object 11 is transferred within the cylindrical member 98. A flange 98a is formed at one axial end of cylindrical member 98 at the downstream side in the transfer direction of object 11, in turn at the central portion side of drum 91, and a pulley 101 is mounted at the outer periphery of cylindrical member 98 at the upstream side in the transfer direction of object 11. A timing belt 103 is mounted on an output shaft of a motor 100 and passes through a cutout (not shown) across the pulley 101 and a pulley 102 so that the rotation of motor 100 is transmitted to the cylindrical member 98 through the pulley 102, timing belt 103 and pulley 101, thereby rotating the cylindrical member 98.

At two diametrically symmetrical positions at the outside end surface of flange 98a at the cylindrical member 98, sensor holders 105, 105 housing therein magnetic field detectors 14 are mounted radially movably through link mechanism 104, 104 respectively, the link mechanisms 104, 104 each providing a leaf spring 106, 106 to push each sensor holder 105, 105 radially inwardly.

A slip ring 107 is fixed between the flange 98a and the mounting plate 96, and a brush 108 in slidable contact with the slip ring 107 is mounted to the mounting plate 96 through a fitting 109 so that a signal from the magnetic field detector 14 in the respective sensor holders 105 is picked up outwardly from the apparatus through the slip ring 107 and brush 108.

Figure 20:
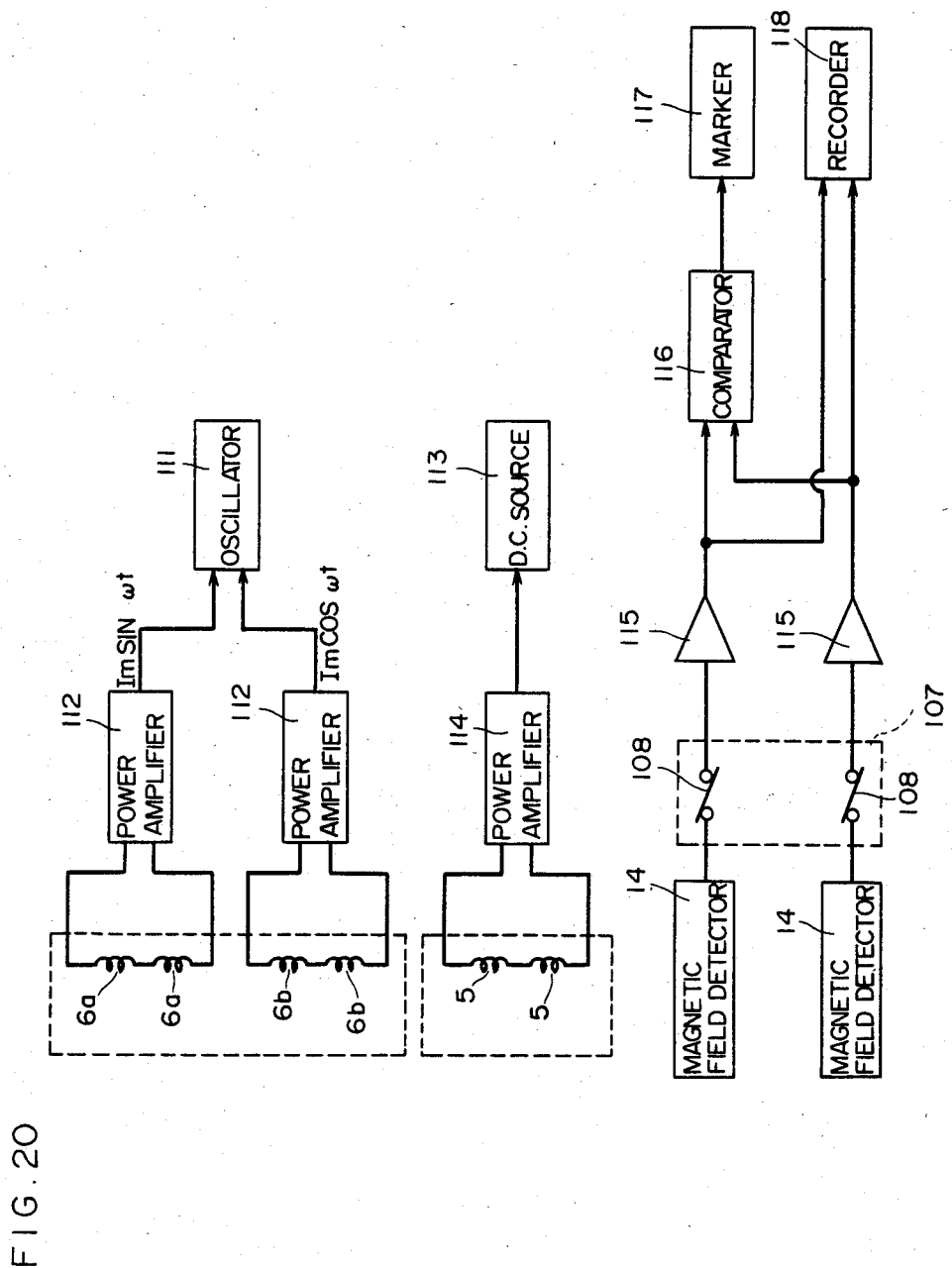
FIG. 20 is a block diagram of an electric circuit of the FIG. 14 embodiment.

FIG. 20 is a block diagram of an example of an electric circuit used in the apparatus constructed as described above. In the same drawing, the coils 6a and 6b wound around the magnetic poles 4a and 4b at the annular electromagnet 4 are supplied with alternating currents $Im \sin \omega t$ and $Im \cos \omega t$ different in phase by $\pi/2$ and generated from an oscillator 111 through power amplifiers 112 respectively and the rotary magnetic field changing in its direction with the lapse of time is formed at the central portion of annular electromagnet 4. Annular solenoids 5, 5 are given a direct current which is fed from a DC source and amplified by a power amplifier 114, thereby producing the axial magnetic field on the outer periphery of object 11. In addition, the exciting current for each annular solenoid 5 is not limited to DC but may be AC.

The magnetic field detectors 14, 14 provided in the sensor holders 105 detect the leakage magnetic field caused by the crack-like flaws existing on the outer periphery of object 11 and extending in the circumferential and axial directions and the turbulence of the magnetic field caused when the eddy current induced by the rotary magnetic field is disturbed by the pit-like surface-flaws or others existing on the outer periphery of the same. Each detection signal is given to the respective amplifier 115 through the brushes 108 and slip ring 107 and amplified by the amplifier 115 and then given to a comparator 116, which compares an output signal of each amplifier, in turn an output signal of each magnetic field detector 14. In a case where a difference between both the signals has the level by which one detector 14 judges the existence of harmful flaw, the marker 117 applies marking at the location of the flaw, the output signal of each amplifier 115 being given to a recorder 118 so that the detection signal from each detector 14 is recorded therein.

In the apparatus of the invention constructed as foregoing, the motor 100 is driven to rotate the cylindrical member 98 within the drum 91 and the object 11 is transferred, then each sensor holder 105 abuts at the lower surface thereof against the outer periphery of object 11 and moves spirally thereon in cooperation with the rotation of cylindrical member 98 and transfer of object 11, thereby carrying out the surface flaw detection. In this case, since each sensor holder 105 is biased toward the center of object 11 through the leaf spring 106, each sensor holder 105 abuts exactly against the outer periphery of object 11 to thereby reliably follow minute vibrations or bends of the object 11.

Alternatively, the magnetic field detector in the aforesaid embodiment may be one or three or more.

Also, the output of each magnetic field detector 14 does not depend on the mutual comparison by comparator 116, but the comparators each setting the comparison reference value may perform the detection of existing flaws.

Although the invention has been described with reference to several embodiments, these embodiments are merely exemplary and not limiting of the invention which is defined solely by the appended claims.

What is claimed is:

1. A method for detecting surface flaws in a metal test surface, comprising the steps of:
   generating a first magnetic field having flux lines parallel to a portion of the test surface;
   generating a second magnetic field having flux lines perpendicular to said portion of the test surface, said first and second magnetic fields producing a resultant magnetic field having flux lines passing through said portion of the test surface;
   providing magnetic field detector means having a single magnetic field sensor adjacent said portion of the test surface; and
   measuring simultaneously with said sensor the magnetic flux leakage caused by surface flaws in said test surface due to the component of said resultant magnetic field which is parallel to said test surface and the magnetic field created by eddy currents in said test surface generated by the component of said resultant magnetic field which is perpendicular to said test surface, said eddy currents being disturbed by surface flaws in said test surface.

2. The method of claim 1, wherein said detector means produces a detection signal which is separated into first and second component signals, said first component signal indicating the magnetic flux leakage due to the component of said resultant magnetic field which is parallel to said test surface, and said second component signal indicating the magnetic field caused by the eddy currents generated by the component of said resultant magnetic field which is perpendicular to said test surface, thereby providing an indication of the type of flaws present in the test surface.

3. The method of claim 2, wherein said first magnetic field is generated by first electromagnetic means driven by a first alternating current, and said second magnetic field is generated by second electromagnetic means driven by a second alternating current, said first and second alternating currents having a relative phase difference.

4. The method of claim 2, wherein said first magnetic field is generated by first electromagnetic means driven by a first alternating current, and said second magnetic field is generated by second electromagnetic means driven by a second alternating current, said first and second alternating currents having a different frequency.

5. A method for detecting surface flaws in a cylindrical metal test object, comprising the steps of:
   generating a first magnetic field having flux lines parallel to the surface of said cylindrical test object;
   generating a second magnetic field having flux lines perpendicular to the surface of said test object, said second magnetic field being generated by an electromagnetic coil means which is excited by an alternating current, said first and second magnetic fields thereby producing a rotating resultant magnetic field having flux lines passing through said test object;
   revolving a magnetic field detector around the outer circumference of said cylindrical test object; and
   measuring simultaneously with said revolving magnetic field detector the magnetic flux leakage caused by flaws in said test object due to the component of said rotary resultant magnetic field which is parallel to the surface of said test object and the magnetic field created by eddy currents in said test object generated by the component of said rotary resultant magnetic field which is perpendicular to the longitudinal axis, said eddy currents being disturbed by flaws in said test object.

6. The method of claim 5, wherein said first magnetic field is generated by a second electromagnetic coil means which is excited by a second alternating current different than said first alternating current.

7. The method of claim 6, wherein said first alternating current has a different phase than said second alternating current.

8. The method of claim 6, wherein said first alternating current has a different frequency than said second alternating current.

9. An apparatus for detecting surface flaws in a metal test surface, comprising:
   first magnetic means for generating a first magnetic field having flux lines parallel to a portion of the test surface;
   second magnetic means for generating a second magnetic field having flux lines perpendicular to said portion of the test surface, whereby said first and second magnetic fields produce a resultant magnetic field having flux lines passing through the portion of the test surface; and
   magnetic field detector means having a single magnetic field sensor for simultaneously detecting both the magnetic flux leakage caused by surface flaws in said test surface due to the component of said resultant magnetic field which is parallel to said test surface and the magnetic field created by eddy currents in said test surface generated by the component of said resultant magnetic field which is perpendicular to said test surface, said eddy currents being disturbed by surface flaws in said test surface, and wherein said detector produces an output which is a function of said magnetic flux leakage due to said parallel component of said resultant magnetic field and said magnetic field created by eddy currents in the test surface generated by said perpendicular component of said resultant magnetic field.

10. The apparatus of claim 9, further including signal processing means for processing said detector output in order to separate the portion of the signal corresponding to said magnetic flux leakage from the portion of the signal corresponding to said magnetic field created by eddy currents in said test surface, thereby to provide an indication of the type of flaws present in said test surface.

11. The apparatus of claim 10, wherein said first magnetic means includes a first electromagnet driven by a first oscillator which generates a first alternating current, and said second magnetic means includes a second electromagnet driven by a second oscillator which generates a second alternating current having a phase different than said first alternating current.

12. The apparatus of claim 10, wherein said first magnetic means includes a first electromagnet driven by a first oscillator which generates a first alternating current, and said second magnetic means includes a second electromagnet driven by a second oscillator which generates a second alternating current having a frequency different than said first alternating current.

13. An apparatus for detecting surface flaws in a metal test surface which is transported through a test station, comprising:

first magnetic means for generating a first magnetic field having flux lines parallel to the test surface, said first magnetic means including cooperating magnetic field generators arranged along the plane of said test surface on opposite sides of said test surface;

second magnetic means for generating a second magnetic field having flux lines perpendicular to the test surface, said first and second magnetic fields producing a resultant magnetic field having flux lines passing through said test surface; said second magnetic means including an air-core coil arranged adjacent said test surface in a direction normal to said test surface, the air-core of said coil extending lengthwise across substantially the entire width of said test surface;

a magnetic field detector arranged within the space defined by the air-core of said coil for simultaneously detecting the magnetic flux leakage caused by surface flaws in said test surface due to the component of said resultant magnetic field which is parallel to said test surface and the magnetic field created by eddy currents on said test surface generated by the component of said resultant magnetic field which is perpendicular to said test surface, said eddy currents being disturbed by surface flaws in said test surface; and means for reciprocating said magnetic field detector along the length of said air-core, thereby scanning said resultant magnetic field across substantially the entire width of said test surface.

14. An apparatus for detecting surface flaws in a metal test surface which is transported through a test station, comprising:

first magnetic means for generating a first magnetic field having flux lines parallel to the test surface, said first magnetic means including cooperating magnetic field generators arranged along the plane of said test surface on opposite sides of said test surface;

second magnetic means for generating a second magnetic field having flux lines perpendicular to the test surface, said first and second magnetic fields producing a resultant magnetic field having flux lines passing through said test surface; said second magnetic means including an air-core coil arranged adjacent said test surface in a direction normal to said test surface, the air-core of said coil extending lengthwise across substantially the entire width of said test surface;

a magnetic field detector arranged within the space defined by the air-core of said coil for detecting said resultant magnetic field and producing an output indicating the magnetic flux leakage caused by surface flaws in said test surface due to the component of said resultant magnetic field which is parallel to said test surface and the magnetic field created by eddy currents on said test surface generated by the component of said resultant magnetic field which is perpendicular to said test surface, said eddy currents being disturbed by surface flaws in said test surface;

means for reciprocating said magnetic field detector along the length of said air-core, thereby scanning said resultant magnetic field across substantially the entire width of said test surface; and signal processing means for separating the output signal of said magnetic field detector into first and second component signals, said first component signal indicating the magnetic flux leakage due to the component of said resultant magnetic field which is parallel to said test surface, and said second component signal indicating the magnetic field caused by the eddy currents generated by the component of said resultant magnetic field which is perpendicular to said test surface, thereby providing an indication of the type of flaws present in the test surface.

15. The apparatus of claim 14, wherein said first magnetic means includes a first electromagnet driven by a first oscillator which generates a first alternating current, and said second magnetic means includes a second electromagnet driven by a second oscillator which generates a second alternating current having a phase different than said first alternating current.

16. The apparatus of claim 14, wherein said first magnetic means includes a first electromagnet driven by a first oscillator which generates a first alternating current, and said second magnetic means includes a second electromagnet driven by a second oscillator which generates a second alternating current having a frequency different than said first alternating current.

17. An apparatus for detecting surface flaws in a cylindrical metal test object, comprising:

first magnetic means for generating a first magnetic field having flux lines parallel to the surface of said cylindrical test object;

second magnetic means for generating a second magnetic field having flux lines perpendicular to the longitudinal axis of said test object, said second magnetic means including an electromagnetic coil means which is excited by an alternating current, said first and second magnetic fields thereby producing a rotary resultant magnetic field having flux lines passing through said test object;

a single magnetic field detector for simultaneously detecting the magnetic flux leakage caused by surface flaws in said test object due to the component of said rotary resultant magnetic field which is parallel to the surface of said test object and the magnetic field created by eddy currents in said test object generated by the component of said rotary magnetic field which is perpendicular to the longitudinal axis, said eddy currents being disturbed by flaws in said test object; and means for revolving said magnetic field detector around the outer circumference of said cylindrical test object.

18. The apparatus of claim 17, wherein said first magnetic means includes an annular core surrounding the outer circumference of said cylindrical test object and having plural pairs of diametrically symmetrical magnetic poles adjacent the circumferential surface of said test object.

19. The apparatus of claim 18, wherein said magnetic field generator produces an output signal indicating the magnetic flux leakage caused by the surface flaws in said test surface due to the component of said resultant magnetic field which is parallel to the surface of said test object and the magnetic field created by eddy currents on said test surface generated by the component of said resultant magnetic field which is perpendicular to the longitudinal axis of said test object; and further comprising signal processing means for separating said output signal into first and second component signals corresponding to the parallel and perpendicular components of said resultant magnetic field, respectively, thereby providing an indication of the type of flaws present in the test surface.

* * * * *